US012605355B2

(12) United States Patent
Pizzocaro et al.

(10) Patent No.: US 12,605,355 B2
(45) Date of Patent: Apr. 21, 2026

(54) HA-PACLITAXEL CONJUGATE FOR TREATMENT OF MESOTHELIOMA

(71) Applicant: FIDIA FARMACEUTICI S.p.A., Abano Terme (IT)

(72) Inventors: Carlo Pizzocaro, Abano Terme (IT); Antonio Rosato, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 648 days.

(21) Appl. No.: 17/916,645

(22) PCT Filed: Apr. 7, 2021

(86) PCT No.: PCT/IB2021/052870
§ 371 (c)(1),
(2) Date: Oct. 3, 2022

(87) PCT Pub. No.: WO2021/205350
PCT Pub. Date: Oct. 14, 2021

(65) Prior Publication Data
US 2023/0138984 A1 May 4, 2023

(30) Foreign Application Priority Data
Apr. 10, 2020 (IT) ........................ 102020000007747

(51) Int. Cl.
| | | |
|---|---|---|
| *A61K 31/337* | (2006.01) | |
| *A61K 9/00* | (2006.01) | |
| *A61K 47/61* | (2017.01) | |
| *A61P 35/00* | (2006.01) | |

(52) U.S. Cl.
CPC .......... *A61K 31/337* (2013.01); *A61K 9/0019* (2013.01); *A61K 47/61* (2017.08); *A61P 35/00* (2018.01)

(58) Field of Classification Search
CPC .... A61K 31/337; A61K 47/61; A61K 9/0019; A61P 35/00
See application file for complete search history.

(56) References Cited

U.S. PATENT DOCUMENTS

| | | | | |
|---|---|---|---|---|
| 7,897,584 B2 * | 3/2011 | De Luca | ................. | A61P 35/00 536/53 |
| 2010/0173865 A1 | 7/2010 | Klostergaard et al. | | |
| 2023/0148151 A1 * | 5/2023 | Campisi | ................. | A61K 47/61 424/181.1 |

FOREIGN PATENT DOCUMENTS

| | | |
|---|---|---|
| WO | WO 2004/035629 A2 | 4/2004 |
| WO | WO 2020/084525 A1 | 4/2020 |

OTHER PUBLICATIONS

Sugarbaker, Surgical Oncology, 33, Jan. 24, 2020, 96-99 (Year: 2020).*

(Continued)

*Primary Examiner* — Andrew D Kosar
*Assistant Examiner* — Phillip Matthew Rzeczycki
(74) *Attorney, Agent, or Firm* — Birch, Stewart, Kolasch & Birch, LLP

(57) ABSTRACT
HA-paclitaxel conjugate for use in the loco-regional treatment of the mesothelioma, i.e., the malignant pleural mesothelioma, pericardial mesothelioma and peritoneal mesothelioma, preferably malignant pleural mesothelioma, and relative pharmaceutical compositions are described.

13 Claims, 1 Drawing Sheet

(56)                    References Cited

OTHER PUBLICATIONS

Vorobiof, Annals of Oncology, 13: 412-415, 2002 (Year: 2002).*
Shigeeda, Oncotarget, 2017, vol. 8, 55, 93729-93740 (Year: 2017).*
Chu et al., "Paclitaxel-loaded expansile nanoparticles improve survival following cytoreductive surgery in pleural mesothelioma xenografts," The Journal of Thoracic and Cardiovascular Surgery, vol. 160, No. 3, Sep. 2020, pp. e159-e168.
Asplund et al., "Hyaluronan Receptors Are Expressed on Human Malignant Mesothelioma Cells but not on Normal Mesothelial Cells", Cancer Research, 1994, vol. 54, No. 16, pp. 4516-4523.
Auzenne et al., "Hyaluronic Acid-Paclitaxel: Antitumor Efficacy against CD44(+) Human Ovarian Carcinoma Xenografts", Neoplasia Jun. 2007, vol. 9, No. 6, pp. 479-486.
Cortes-Dericks et al., "CD44 and its ligand hyaluronan as potential biomarkers in malignant pleural mesothelioma: evidence and perspectives", Respiratory Research 2017, vol. 18, No. 1, ART. 58., pp. 1-12.
Galer et al., "Hyaluronic acid-paclitaxel conjugate inhibits growth of human squamous cell carcinomas of the head and neck via a hyaluronic acid-mediated mechanism", Oral Oncology, 2011, vol. 47, pp. 1039-1047.

International Preliminary Examination Report (PCT/IPEA/409), issued in PCT/IB2021/052870, dated Jul. 13, 2022.
International Search Report, issued in PCT/IB2021/052870, dated Jun. 10, 2021.
Lee et al., "Metronomic Activity of CD44-Targeted Hyaluronic Acid-Paclitaxel in Ovarian Carcinoma"; Clinical Cancer Research, 2012, vol. 18, No. 15, pp. 4114-4121.
Luo et al., "A Hyaluronic Acid-Taxol Antitumor Bioconjugate Targeted to Cancer Cells", Biomacromolecules 2000, vol. 1, No. 2, pp. 208-218.
Mittapalli et al., "Paclitaxel-Hyaluronic NanoConjugates Prolong Overall Survival in a Preclinical Brain Metastases of Breast Cancer Model", Molecular Cancer Therapeutics, 2013, vol. 12, No. 11, pp. 2389-2399.
Sasai et al., "Novel Hyaluronan Formulation Enhances the Efficacy of Boron Neutron Capture Therapy for Murine Mesothelioma", Anticancer Research, 2016, vol. 36, No. 3, pp. 907-911.
Ween et al., "Role of Versican, Hyaluronan and CD44 in Ovarian Cancer Metastasis", International Journal of Molecular Sciences, 2011, vol. 12, No. 2, pp. 1009-1029.
Written Opinion of the International Searching Authority, issued in PCT/IB2021/052870, dated Jun. 10, 2021.

* cited by examiner

DAY 139

HA-PACLITAXEL CONJUGATE FOR TREATMENT OF MESOTHELIOMA

OBJECT OF THE INVENTION

The present invention describes the conjugate of hyaluronic acid to paclitaxel and the composition comprising or consisting of such conjugate associated with pharmacologically acceptable diluents/excipients, for use in the loco-regional treatment of mesothelioma, particularly malignant pleural.

FIELD OF THE INVENTION

The term serous membrane or tunic means a particular tissue formed by a simple pavement epithelium known as mesothelium sustained by an underlying connective, vascularized and innervated tissue. The function of the serosa is to cover organs of the thorax and the abdomen, it is therefore distinguished in visceral, the layer or sheet covering the organ, and parietal, the outer layer or sheet facing and lining the wall; between the two layers a virtual cavity known as serous cavity containing moderate quantities of serous fluid produced by mesothelium is identified, while the underlying connective tissue provides blood and nerve supply being the mesothelium completely free of blood vessels and nerves.

Based on the organ or the wall covered, a serosa is distinguished in covering the heart and the mediastinum, known as pericardium;

covering the lungs and the thoracic wall, known as pleura;

covering the abdominal wall and the organs contained therein, known as peritoneum;

covering the testicle, known as vaginal tunic;

lastly covering uterus, known as perimetrium.

The pleura is therefore a double-wall serous membrane covering and adhering to the inner wall of the thorax with its parietal sheet, and to the distal wall of each lung with its visceral sheet.

The neoplasm arising from the mesothelium cells is called mesothelioma and can therefore originate from the thorax, the abdomen, and, very rarely, in the cavity around the heart and in the membrane covering the testicles.

The mesothelioma is a rare tumor representing less than 1% of all oncological diseases even if its incidence is constantly rising with 2.2 cases per million people; it is a very aggressive neoplasm and the most common form is the one affecting the pleura: in this case it is defined as malignant pleural mesothelioma (MPM) which represents about 80% of all mesotheliomas, peritoneal, pericardial and testicles mesotheliomas being more rare; more frequent in males, the incidence of the mesothelioma increases with age with 75% of patients over 65 years of age.

The most important risk factor for the pleural mesothelioma (but in general for all types of mesothelioma) is represented by asbestos exposure: indeed, the majority of these tumors affects people who came into contact with this substance mainly on the workplace, or living with people who work it. Asbestos is a natural mineral with a fibrous structure belonging to the chemical class of the silicate, and, due to its peculiar resistance to heat, it has been widely used in the past for roof sealing and insulation (in a material known as Eternit), ships and trains, in construction (roof tiles, floors, paints . . . ), in firefighter suits, in cars (mechanical components and paints) and in other sectors.

When this mineral is fragmented, for example during the mineral extraction and processing or for wear of the material containing it, a very fine powder remaining suspended in the air even for a long time is produced, and it is easily inhaled. This powder can damage the mesothelial cells causing (in some cases) cancer even decades after exposure. Other risk factors for the mesothelioma are:

simian virus SV40, used in polio vaccines between 1955 and 1963;

thorium dioxide used between the 1920's and 1950's;

radiations to thorax and abdomen.

(Sekido Y. et al., *Carcinogenesis,* 2013, 34 (7): 1413-9; Remon J. Et al., Cancer Treat Rev, 2013, 39 (6): 584-91).

The treatment of mesothelioma depends in general on the tumor site, the stage of disease, patient's age and general health status. Standard treatment options include surgery, radiotherapy and chemotherapy.

In general, in stage I MPM, tumor is confined to parietal pleura and it is not present in lymph nodes; in stage II, it also affects visceral pleura, lung or diaphragm; in stage III, tumor has invaded the first layer of the thoracic wall, part of the mediastinum or a point on the thoracic wall; it can also affect the outer surface of the pericardium and lymph nodes on one of the two sides of the thorax; in stage IV, tumor has reached other organs (metastasis) such as liver, brain, bones or lymph nodes on both sides of the thorax.

According to recent clinical studies, chemotherapy can be considered as the only treatment capable of prolonging (at least partly) the patient's life, improving although limitedly, its quality. Drugs approved for such use, commonly used alone (or more often in combination), are pemetrexed (Alimta®), cisplatin and raltitrexed (Tomudex®); mitomycin, vinorelbine and gemcitabine are instead still in the experimental stage, however, the malignant pleural mesothelioma MPM (like all other forms of mesothelioma) is generally refractory to such treatments and results obtained are modest (Stahel R A. et al, *Ann Oncol.,* 2015, 26 (8): 1649-60). Chemotherapeutic agents have also very debilitating side effects and, therefore, there are many uncertainties and even contraindications to the opportunity to start chemotherapy at the diagnosis or at the onset of early symptoms of MPM.

To date there is no therapy able to treat or to significantly slow down the malignant pleural mesothelioma, it is only possible to reduce its tumor mass and, consequently, to prolong patient's survival by few months. The most successful procedures involve the early stages of the disease and combine pre-operative chemotherapy with surgical procedure and subsequent post-operative radiotherapy. However, such approach can be proposed only to very young patients without concomitant diseases. In any case, appropriate studies demonstrating an effective benefit in terms of prolonging life are not yet available. Unfortunately, the mean survival time after diagnosis is still 6-9 months without chemotherapy, 12 months with such therapy.

In view of the above reasons, new pharmaceutical approaches are being tested such as, for example, immunotherapy or treatments directly aimed at the treatment of the neoplasm by using drug delivery systems. Indeed, such systems can transport drugs directly to the tumor site allowing the treatment of the neoplasm at lower doses of chemotherapeutic agent than a systemic treatment, therefore with a lower toxicity and resulting in better patient's quality of life, but especially, such systems, when really effective, are capable of significantly increasing life expectancy of a cancer patient.

Hyaluronic acid is one of the polymers (and polysaccharides) used in the formation of such drug delivery systems both as associated polymer and as polymer chemically bound to numerous categories of antineoplastic drugs (Liao Y H. et al., *Drug Deliv.*, 2005, 12 (6): 327-42). The HA is a hetero-polysaccharide composed by alternating residues of D-glucuronic acid and N-acetyl-D-glucosamine, it is a linear chain polymer with a molecular weight comprised between 50,000 and 13×10⁶ Da, depending on the source from which it is obtained and preparation methods used. It is naturally present in the pericellular gels, in the essential substance of the connective tissue of vertebrate organisms, in the joint synovial fluid, in the vitreous humor and in the umbilical cord. The HA plays an important role in the biological organism, for example as mechanical support of cells of many tissues such as skin, tendons, muscles and cartilage, being the main component of the extracellular matrix, but also acting further functions such as tissue hydration, cell lubrication, migration and differentiation (Weigel P. et al., J Theoretical Biol, 1986:219-234).

Among the drug delivery systems using the HA, the conjugate of paclitaxel with hyaluronic acid (HA) derivatized with hydrazide molecules bound to the carboxyl group of the HA through amide bond (Luo Y. et al., *Biomacromolecules*, 2000, 1(2):208-218) is known: however, to date there are no preclinical or clinical trials that have demonstrated the effectiveness of such derivate.

The system constituted by the HA conjugated to paclitaxel by a spacer (EP2045270) is also known: such conjugate has been tested both in in vitro (and particularly in bladder cancer, breast cancer and ovarian cancer cells) trials proving to be at least as much active as the reference medicine, and in in vivo clinical protocols (currently ongoing) on the treatment of non-invasive bladder cancer (IT 102018000009731).

The conjugation with HA makes paclitaxel soluble and the administration of paclitaxel can therefore happen without the multiple phenomena of hypersensitivity that normally occur during the use of the drug due to the presence of Cremophor EL, the solubilization solvent currently used in the standard clinical protocols, whose presence is necessary precisely because the active ingredient is liposoluble (Taxol®). Paclitaxel is an anti-cancer agent (Huizing M T et al., *Cancer Inv.*, 1995, 13:381-404) performing its antiproliferative action acting on the organization of microtubules of the cellular cytoskeletal system preventing it from the normal reorganization during the mitotic division (Manfredi J J et al., *J Cell Biol*, 1982, 94:688-696); its main therapeutic indications are the treatment of breast cancer, lung cancer, ovarian cancer, bladder cancer, prostate and endometrial cancer, and not comprising the treatment of mesothelioma.

In the HA-paclitaxel conjugate, the bond between paclitaxel and HA allows the drug to directly reach the membrane surface of the tumor cell characterized by an overexpression of HA receptor, CD44 (Isacke C M. et al., *Int J Biochem Cell Biol*, 2002, 34:718-21). Accordingly, the paclitaxel conjugated to HA is capable to specifically binding to CD44 of the tumor cell thus being capable of entering into cell cytoplasm wherein, through the hydrolysis of the bond drug/HA, it is activated. This drug selective transport mechanism is defined of "targeting" to the target cell.

DETAILED DESCRIPTION OF THE INVENTION

Figure 1:
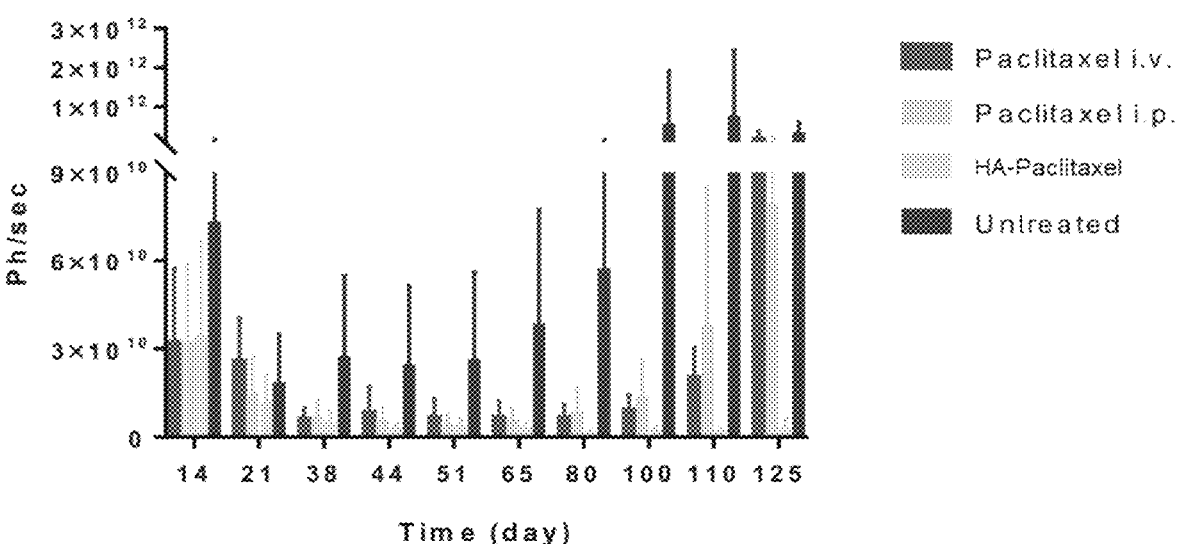
FIG. 1 shows a line graph of luminescence (photons/sec) vs survival days. Untreated animals reach ~1×10¹² by day 100. Two non-conjugated paclitaxel groups remain around ~1×10¹¹, lower than control. HA-paclitaxel conjugate shows a sharp drop from day 14 to day 125, remaining near zero. The conjugate data appear as the third of four columns for each time point.

Object of the present invention is the HA-paclitaxel conjugate for use in the loco-regional treatment of mesothelioma, therefore malignant pleural mesothelioma, pericardial mesothelioma and peritoneal mesothelioma, in particular for use in the treatment of MPM, wherein such HA-paclitaxel conjugate has an ester bond between the carboxyl of hyaluronic acid (HA) and a spacer, in turn bound by an ester bond through its carboxyl to the hydroxyl group to the carbon C2' of paclitaxel, wherein the spacer introduced is the 4-bromobutyric acid, and wherein the derivatization degree of paclitaxel in the HA-paclitaxel conjugate is within the range that varies from 15% to 21% weight/weight (w/w), and preferably from 16% to 20% w/w.

Hereinafter in the present description, derivatization (or esterification) degree of the above-mentioned conjugate means the weight percentage of paclitaxel with respect to the weight of the HA-paclitaxel conjugate.

Therefore, 100 mg of conjugate with derivatization degree comprised between 15% and 21% w/w, will contain 15 mg, 16 mg, 17 mg, 18 mg, 19 mg, or 20 mg, or 21 mg of chemotherapeutic paclitaxel depending on the derivatization degree indicated (to further exemplify this, the derivatization degree at 20% w/w contains 20 mg of paclitaxel per 100 mg of conjugate); it is however obvious to the skilled person that, at the end of such industrial synthesis processes, a small variation in the weight ratios between the molecules can occur, therefore hereinafter the Applicant, describing and claiming the derivatization range of the above-mentioned conjugate comprised between 15% and 21% w/w, intends to claim all the reported percentage values comprising ±1%: by way of example, the degree of 20% w/w is accordingly to be intended as 20%±1%.

The HA-paclitaxel conjugate for the above-claimed use was prepared according to a synthesis process known in the state of the art as described in EP2045270 and, for the derivatization degree of 20%, improved in IT 102018000009731.

In broad terms, in such synthesis process of the above-mentioned conjugate, the spacer/linker 4-bromobutyric acid is introduced between hyaluronic acid and paclitaxel through the formation of the ester bond between the carboxyl of hyaluronic acid and the spacer, said spacer being in turn bound (always by ester bond) through its carboxyl to the hydroxyl group to the carbon C2' of paclitaxel, more precisely the carboxyl group of the 4-bromobutyric acid, through activation with an activating agent and in the presence of a catalyst, forming an ester bond with the hydroxyl function to C2' carbon of paclitaxel; subsequently the intermediate thus obtained reacts with a salt of HA, under suitable conditions, giving rise to the nucleophilic substitution of COO-of HA to the carbon bound to the bromine of the spacer-linker. In this way, the ester bond is formed between the HA and the spacer-linker previously bound to paclitaxel.

The HA used for the synthesis of such HA-paclitaxel conjugate can derive from any source, for example by extraction from rooster combs (EP0138572, WO2018020458), by fermentative route (EP0716688), or by biotechnological route (EP2614088, EP2614087) and having a weight average molecular weight (MW) ranging from 400 to $3\times10^6$ Da, particularly from 400 to $1\times10^6$ Da, even more particularly from 140.000 to 250.000 Da (weight average molecular weight means the one calculated with the "intrinsic viscosity" method (Terbojevich et al., *Carbohydr Res*, 1986, 363-377).

Preferably, the HA used for the synthesis of the HA-paclitaxel conjugate for use according to the present invention is a fermentative HA with an average weight MW comprised between 140.000 and 250.000 Da.

Preferably, the HA-paclitaxel conjugate for use according to the present invention has an average derivatization degree of 20% w/w.

A further object of the present invention is also a pharmaceutical composition consisting essentially of the HA-paclitaxel conjugate described above, associated with pharmacologically acceptable diluents/excipients, preferably a pharmaceutical composition formulated in sterile, isotonic water, containing 5% w/v of glucose for use in the loco-regional treatment of mesothelioma, therefore of the malignant pleural mesothelioma, pericardial mesothelioma and peritoneal mesothelioma, preferably for use in the treatment of malignant pleural mesothelioma.

Such pharmaceutical composition is thus formulated as, sterile and isotonic, aqueous solution, consisting essentially of the conjugate itself.

The Applicant describes and claims the conjugate for the use above in the loco-regional treatment of all the known and above-cited mesothelioma forms and preferably the use in the loco-regional treatment of MPM, since the synergistic effect of HA and paclitaxel chemically bound in the conjugate object of the invention, both in tests carried out in vitro and in vivo vs non-conjugated paclitaxel, is demonstrated below.

The results obtained, both in terms of $IC_{50}$ for in vitro studies, and expressed as bioluminescence values as index of the tumor mass size in the treated animals, surprisingly demonstrate the pharmacological potency of the HA-paclitaxel conjugate and the synergistic effect of the hyaluronic acid conjugate to chemotherapeutic agent vs non-conjugated paclitaxel in the treatment of mesothelioma, in particular of the pleural mesothelioma.

Such result is even more important considering the loco-regional treatment intended to be claimed for such conjugate: this administration route, i.e., intrapleural, or intraperitoneal and intrapericardial, in fact allows the administration of the conjugate directly to the tumor mass at lower/analogous doses or even higher than the reference chemotherapeutic agent, in order to obtain a therapeutic effectiveness higher than the drug reference maintaining a high safety profile.

The HA-paclitaxel conjugate remains indeed as depot in the administration cavity directly in contact with the tumor mass for prolonged times, thus allowing its concentration mainly at the action site (and not at systemic level), maximizing in this way the interaction with the tumor without damaging the surrounding tissue, reducing the side effects. The drug selective transport mechanism to the tumor cell for the high expression of CD44 on the surface of such cells is also used, through the "targeting" action of hyaluronic acid.

Animal testing described below especially demonstrates the effectiveness in vivo of such HA-paclitaxel conjugate, wherein such effectiveness will result in humans not only in the increasing of sick-person survival, but also in a better quality of life for a category of patients which, as previously reported, have an extremely limited life expectancy even after the chemotherapy treatment.

Example 1

Cytotoxicity of the HA-Paclitaxel Conjugate in Mesothelioma Cells Vs Paclitaxel

Experimental procedure: the cytotoxic activity of the HA-paclitaxel conjugate object of the invention has been evaluated in vitro by performing the MTT assay on cell lines of human mesothelioma commercially available H2052, H28 and H2452, wherein all such cell lines express CD44 receptor for hyaluronic acid. The conjugate used for such trial has been prepared according to IT 102018000009731, therefore with an average derivatization degree of 20% w/w starting from a fermentative HA with an average weight MW comprised between 140.000 and 250.000 Da.

Cells were plated (Day 0) in multiwell plate of 96 flat-bottomed wells (3000 cells per well) in EMEM culture medium (SIGMA, Saint Louis, Missouri, USA) and subsequently they were incubated for 24 hours at 37° C. in the presence of 5% $CO_2$. The next day (Day 1) the medium was changed providing the cells with fresh EMEM medium containing alternatively paclitaxel, as a control, or the HA-paclitaxel conjugate in suitable dilutions. After two days of incubation (Day 3), each well containing the cells was treated with 100 μl of reagent 3-2,5-diphenyltetrazolium bromide (5 mg/ml in DMEM) for 90 minutes. Subsequently, at the removal of the reagent from each well and the corresponding addition of 100 μl of DMSO, was measured the absorbance of the formazan salt (blue, produced by the reaction of breaking the MTT tetrazolium ring, performed by the mitochondrial enzyme "succinate dehydrogenase" present only in the viable cells) at the wavelength of 570 nm by a multiplate reader. Such MTT assay, widely known to the skilled person, allows to evaluate the viability of the cells treated with the conjugate vs those treated with paclitaxel alone and therefore to determine the susceptibility of the above-mentioned cells to the tested samples. Data were then normalized to control and the $IC_{50}$ value was calculated in ug/ml of conjugate (expressed in terms of paclitaxel-equivalents) compared to non-conjugated paclitaxel.

Results are summarized in the table below where it is clearly evident that the HA-paclitaxel conjugate shows an activity (therefore an antitumor effectiveness) up to 65-70 times greater than the one of non-conjugated paclitaxel. Normalized $IC_{50}$, μg/ml

|  | HA-paclitaxel | paclitaxel |
| --- | --- | --- |
| H2452 | 0.0122 | 0.8 |
| H28 | 0.033 | 0.787 |
| H2052 | 0.0342 | 0.225 |

Example 2

In Vivo Trial in Immunodeficient NSG Mice

The cell lines of human mesothelioma H2052 were transduced with a lentiviral vector (method by which the genes can be inserted into cells using the lentivirus) containing a bidirectional promoter allowing the high and coordinated expression of two reporter genes for the synthesis of luciferase and eGFP (enhanced Green Fluorescent Protein), as described in Amendola et al., Nat Biotechnol 2005, 23:108-16: luciferase is an enzyme that catalyzes the oxidation of luciferin which oxidizing emits energy (electrons) in the form of light radiation and such reaction has an ultra-high sensitivity; the eGFP derives from the jellyfish *Aequorea victoria*, and it is capable of emitting bright green light when exposed to certain wavelengths; both such proteins are used below as a "marker system" for human mesothelioma cells H2052 transduced as above, in order to identify the tumor mass that is formed in animals injected with such cells and to determine its dimensions and the growth over time through suitable bioluminescence sensor.

Cells were incubated for 6 hours in a mixture of complete medium (RPMI+10% FBS, 1% HEPES, L-glutamine and penicillin/streptomycin) containing the above-mentioned vector and protamine sulphate. At the end of 6 hours of incubation, supernatants were re-integrated with complete medium. After 5 days, the effect of the transduction was evaluated through flow cytometry.

Cells were then expanded and sub-divided in order to isolate the population with the higher expression of reporter genes. Such cells transduced and selected were then injected into the peritoneum of NSG mice, (i.e., immunodeficient that therefore allow engraftment of a wide range of human cancer cells), 10 mice/sample, which were then subjected to the following treatment:

1° sample treated with HA-paclitaxel 40 mg/Kg, by intraperitoneal (ip) loco-regional administration;

2° sample treated with paclitaxel 10 mg/Kg, by intravenous administration (iv) for 3 treatments, switching then to ip administration due to the very poor tolerability of iv treatment with paclitaxel of NSG mice;

3° sample treated with paclitaxel 10 mg/Kg, by intraperitoneal (ip) loco-regional administration;

4° not-treated sample;

by weekly administration for 10 weeks.

All treated animals were monitored through detection of bioluminescence emitted by their tumor zone treated with HA-paclitaxel conjugate, in order to assess over time, the dimension (and therefore the growth) of the tumor with reference to animals untreated with any chemotherapeutic agent and to those treated with non-conjugated paclitaxel.

Results have been plotted in FIG. 1 where it is clearly evident that the luminescence (expressed in photons/sec, Ph/sec) of the untreated animals reaches average values in the order of magnitude of $1\times10^{12}$ on the 100° day of survival, indicating therefore the dimension/growth reached by the untreated tumor; 2° and 3° sample, both treated with non-conjugated paclitaxel with different ways of administration, are compared vs such controlled sample: this comparison indicates an important result for both, since the average luminescence values reached prove to be in the order of magnitude of $1\times10^{11}$, therefore lower than untreated, indicating a reduced tumor mass compared to the control.

However, the result of the HA-paclitaxel conjugate is entirely surprising since from the 14° to the 125° day of survival, the luminescence drops dramatically and remains negligible over time. These completely unexpected data show the significant reduction in the tumor both vs the untreated control and vs animals treated with non-conjugate chemotherapeutic agent administered iv and ip, demonstrating the total effectiveness of the conjugate itself. In FIG. 1 luminescence datum related to the HA-paclitaxel conjugate is represented in the third out of the four columns corresponding to the days of survival reported in abscissa.

Figure 2:
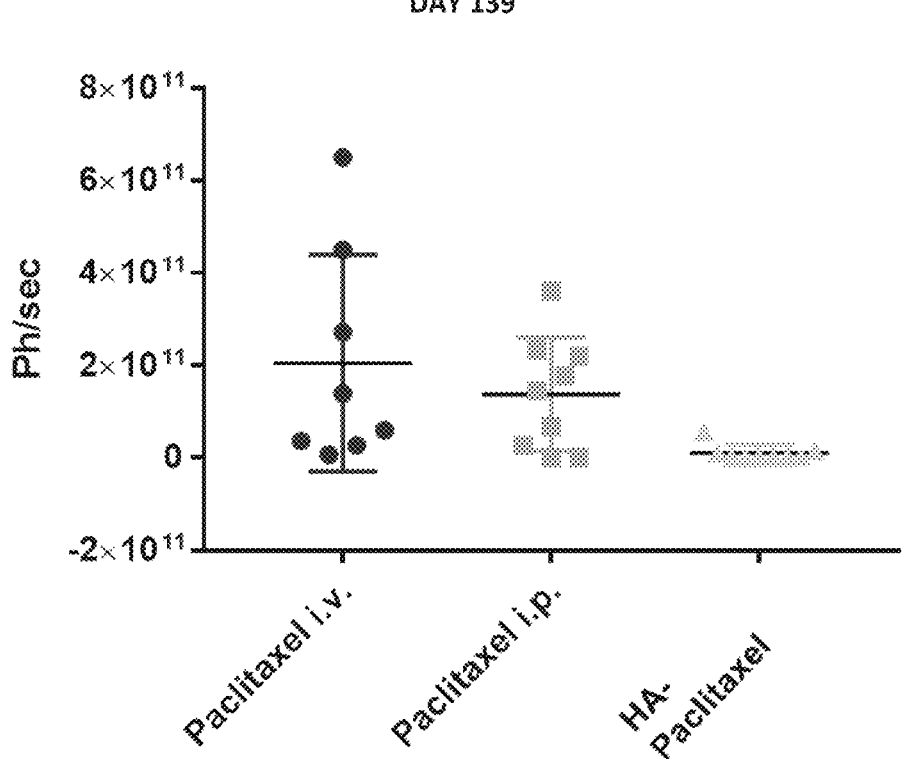
FIG. 2 shows a dot plot of luminescence (photons/sec) at day 139 for three treatment groups. Individual data points are shown with mean and error bars. Non-conjugated paclitaxel (IV and IP) groups cluster around ~1-2×10¹¹. HA-paclitaxel conjugate group shows values near zero, indicating minimal tumor mass.

In FIG. 2 data obtained after 139 days of observation are reported instead, where it is clearly evident that bioluminescence detection in Ph/sec emitted by their treated tumor zone and therefore representative of the tumor mass, remains around $1\text{-}2\times10^{11}$ in mice treated with non-conjugated paclitaxel, while in mice treated with the conjugate such value is extremely lower and close to 0, indicating therefore an almost complete reduction in the tumor mass.

Through the results discussed above, the Applicant demonstrated the pharmacological potency and therefore the effectiveness of the HA-paclitaxel conjugate in the loco-regional treatment of mesothelioma, particularly of MPM, peritoneal and pericardial mesothelioma, since it is capable of determining the significant reduction of tumor mass, accordingly increasing patient survival and his quality of life.

The invention claimed is:

1. A method of loco-regional treatment of mesothelioma which comprises administering to a patient a hyaluronic acid-paclitaxel (HA-paclitaxel) conjugate, wherein said HA-paclitaxel conjugate has an ester bond between the carboxyl of HA and a spacer, in turn bound by an ester bond through its carboxyl to the hydroxyl group to the carbon C2' of paclitaxel, wherein the spacer introduced is 4-bromobutyric acid and wherein the derivatization degree of paclitaxel in the HA-paclitaxel conjugate is within the range that varies from 15% to 21% weight/weight (w/w), and wherein the mesothelioma is malignant pleural mesothelioma, pericardial mesothelioma or peritoneal mesothelioma.

2. The method according to claim 1, wherein the mesothelioma is malignant pleural mesothelioma.

3. The method according to claim 1, wherein the administration route is intrapleural, or intraperitoneal or intrapericardial.

4. The method according to claim 1, wherein the derivatization degree of paclitaxel in the HA-paclitaxel conjugate ranges from 16% to 20% w/w.

5. The method according to claim 1, wherein the derivatization degree of paclitaxel in the HA-paclitaxel conjugate is equal to 20% w/w.

6. The method according to claim 1, wherein HA used for the synthesis of the HA-paclitaxel conjugate is a fermentative HA with an average weight MW ranging from 140,000 to 250,000 Da.

7. The method according to claim 2, wherein the administration route is intrapleural.

8. The method according to claim 2, wherein the derivatization degree of paclitaxel in the HA-paclitaxel conjugate ranges from 16% to 20% w/w.

9. The method according to claim 3, wherein the derivatization degree of paclitaxel in the HA-paclitaxel conjugate ranges from 16% to 20% w/w.

10. The method according to claim 2, wherein the derivatization degree of paclitaxel in the HA-paclitaxel conjugate is equal to 20% w/w.

11. The method according to claim 3, wherein the derivatization degree of paclitaxel in the HA-paclitaxel conjugate is equal to 20% w/w.

12. The method according to claim 4, wherein the derivatization degree of paclitaxel in the HA-paclitaxel conjugate is equal to 20% w/w.

13. The method according to claim 2, wherein HA used for the synthesis of the HA-paclitaxel conjugate is a fermentative HA with an average weight MW ranging from 140,000 to 250,000 Da.

* * * * *